(12) United States Patent
Tanino et al.

(10) Patent No.: US 11,280,920 B2
(45) Date of Patent: Mar. 22, 2022

(54) SCINTILLATOR PANEL, X-RAY DETECTOR USING SAME, AND X-RAY FLUOROSCOPY DEVICE

(71) Applicant: Toray Industries, Inc., Tokyo (JP)

(72) Inventors: Takahiro Tanino, Otsu (JP); Sho Miyao, Otsu (JP); Natsumi Shinohara, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 17/421,075

(22) PCT Filed: Dec. 17, 2019

(86) PCT No.: PCT/JP2019/049412
§ 371 (c)(1),
(2) Date: Jul. 7, 2021

(87) PCT Pub. No.: WO2020/153049
PCT Pub. Date: Jul. 30, 2020

(65) Prior Publication Data
US 2022/0043170 A1   Feb. 10, 2022

(30) Foreign Application Priority Data
Jan. 24, 2019   (JP) .............................. JP2019-009913

(51) Int. Cl.
*G01T 1/20* (2006.01)
*G01T 1/208* (2006.01)
(Continued)

(52) U.S. Cl.
CPC ............ *G01T 1/208* (2013.01); *G01T 1/2006* (2013.01); *H01L 27/14658* (2013.01); *H04N 5/32* (2013.01)

(58) Field of Classification Search
CPC . G01T 1/208; G01T 1/2006; H01L 27/14658; H04N 5/32
See application file for complete search history.

(56) References Cited

U.S. PATENT DOCUMENTS

| 4,689,487 A * | 8/1987 | Nishiki ................. G01T 1/2018 250/361 R |
| 2013/0083891 A1* | 4/2013 | Oyaizu .............. C09K 11/7771 378/57 |

(Continued)

FOREIGN PATENT DOCUMENTS

| JP | 60149594 A | 8/1985 |
| JP | 2000105299 A | 4/2000 |

(Continued)

OTHER PUBLICATIONS

International Search Report and Written Opinion for International Application No. PCT/JP2019/049412, dated Mar. 3, 2020, 6 pages.

*Primary Examiner* — Kiho Kim
(74) *Attorney, Agent, or Firm* — Ratnerprestia

(57) ABSTRACT

A problem addressed by the present invention is to provide a scintillator panel having excellent sensitivity and sharpness, and the spirit of the present invention is that the scintillator panel includes a base plate and a scintillator layer containing a binder resin and a phosphor, said scintillator layer further containing a compound represented by the following general formula (1) and/or a salt thereof;

[Chem. 1]

(1)

(Continued)

(wherein, in the general formula (1), R represents a $C_{1-30}$ hydrocarbon group; m represents an integer of 1 to 20; n represents 1 or 2; and when n is 2, a plurality of Rs may be the same or different).

6 Claims, 1 Drawing Sheet

(51) Int. Cl.
    *H01L 27/146*     (2006.01)
    *H04N 5/32*     (2006.01)

(56) References Cited

U.S. PATENT DOCUMENTS

| | | | |
|---|---|---|---|
| 2013/0092828 A1 | 4/2013 | Perna et al. | |
| 2016/0282483 A1* | 9/2016 | Arimoto | G03F 7/2022 |
| 2017/0158957 A1* | 6/2017 | Hong | G02B 6/0023 |

FOREIGN PATENT DOCUMENTS

| | | | | |
|---|---|---|---|---|
| JP | 2000121799 A | | 4/2000 | |
| JP | 2005125764 A | | 5/2005 | |
| JP | 2011141134 A | | 7/2011 | |
| JP | 2015110726 A | * | 6/2015 | C09B 57/004 |

\* cited by examiner

SCINTILLATOR PANEL, X-RAY DETECTOR USING SAME, AND X-RAY FLUOROSCOPY DEVICE

CROSS REFERENCE TO RELATED APPLICATIONS

This is the U.S. National Phase application of PCT/JP2019/049412, filed Dec. 17, 2019 which claims priority to Japanese Patent Application No. 2019-009913, filed Jan. 24, 2019, the disclosures of each of these applications being incorporated herein by reference in their entireties for all purposes.

FIELD OF THE INVENTION

The present invention relates to a scintillator panel, an X-ray detector using the same, and an X-ray fluoroscopic device.

BACKGROUND OF THE INVENTION

X-ray images taken using film have conventionally been used widely in medical practice. However, an X-ray image taken using film is analog image information, and thus, in recent years, digital radiation detection devices such as a flat panel radiation detector (FPD) have been developed.

An FPD, which is based on an indirect conversion method, involves using a scintillator panel to convert X-rays into visible light. Such a scintillator panel has a scintillator layer containing a phosphor such as gadolinium oxysulfide (GOS), and the phosphor emits light when exposed to X-rays. The light emitted from the scintillator panel is converted into an electric signal using a sensor (photoelectric conversion layer) having a thin-film transistor (TFT) or a charge-coupled device (CCD), whereby the X-ray information is converted into digital image information.

It is desirable that an X-ray detector, which is a radiation detection device utilizing X-rays as radiation, has high sensitivity to a low dose of radiation, and in addition, high sharpness. For example, medical practice needs to minimize the dose of radiation to which a subject is exposed by X-ray diagnosis or the like. However, decreasing the dose of radiation, that is, the dose of incident X-rays, onto an X-ray detector causes the light emission luminance of the phosphor in the scintillator panel to be relatively lower. Because of this, the scintillator panel needs to have high luminance, that is, high sensitivity, even to a low dose of radiation.

Here, it is general that the more the amount of the phosphor per unit exposure area in the scintillator layer, the higher the sensitivity of the scintillator panel. However, simply increasing the amount of the phosphor increases the thickness of the scintillator layer in proportion to that amount, and thus, light emitted in the scintillator layer is more likely to be scattered before reaching the sensor, resulting in a decrease in the sharpness. Accordingly, in order to obtain a scintillator panel having both high sensitivity and high sharpness, it is important to maximize the amount of the phosphor without increasing the thickness, that is, to pack the phosphor densely.

One method proposed as a technique for packing a phosphor densely involves adding a coupling agent or a surfactant to the scintillator layer. For example, there is a report that containing a phosphoric acid coupling agent or a fluorine surfactant enables the phosphor to have an increased packing density, thus making it possible to obtain a radiological image converting panel having high sensitivity and high sharpness (see Patent Literature 1 and 2).

PATENT LITERATURE

Patent Literature 1: JP2000-105299A
Patent Literature 2: JP2000-121799A

SUMMARY OF THE INVENTION

Even with the techniques described in these articles of literature, however, the scintillator panel only has insufficient sensitivity and sharpness.

In view of the above-mentioned problem, an object of the present invention is to provide a scintillator panel having excellent sensitivity and sharpness.

To solve the above-mentioned problem, exemplary embodiments of the present invention mainly has the below-mentioned constituent. That is, a scintillator panel having a base plate and a scintillator layer containing a binder resin and a phosphor, the scintillator layer further containing a compound represented by the following general formula (1) and/or a salt thereof.

[Chem. 1]

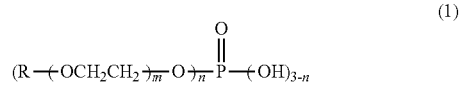
(1)

(In the general formula (1), R represents a $C_{1-30}$ hydrocarbon group. m represents an integer of 1 to 20. n represents 1 or 2. When n is 2, a plurality of Rs may be the same or different.)

A scintillator panel according to embodiments of the present invention has excellent sensitivity and sharpness.

DETAILED DESCRIPTION OF EMBODIMENTS OF THE INVENTION

A scintillator panel according to embodiments of the present invention has at least a base plate and a scintillator layer. The scintillator layer absorbs the energy of radiation such as incident X-rays, and emits, for example, electromagnetic waves in the wavelength range of from 300 nm to 800 nm, that is, light in the range of from ultraviolet light to infrared light with visible light in the center therebetween. The scintillator layer contains at least a binder resin, a phosphor, a compound represented by the below-mentioned general formula (1), and/or a salt thereof. The binder resin has the effect of binding a plurality of phosphor particles to fix the relative position of the phosphor particles in the scintillator layer. The phosphor has the effect of absorbing the energy of radiation such as X-rays to emit light.

Figure 1:
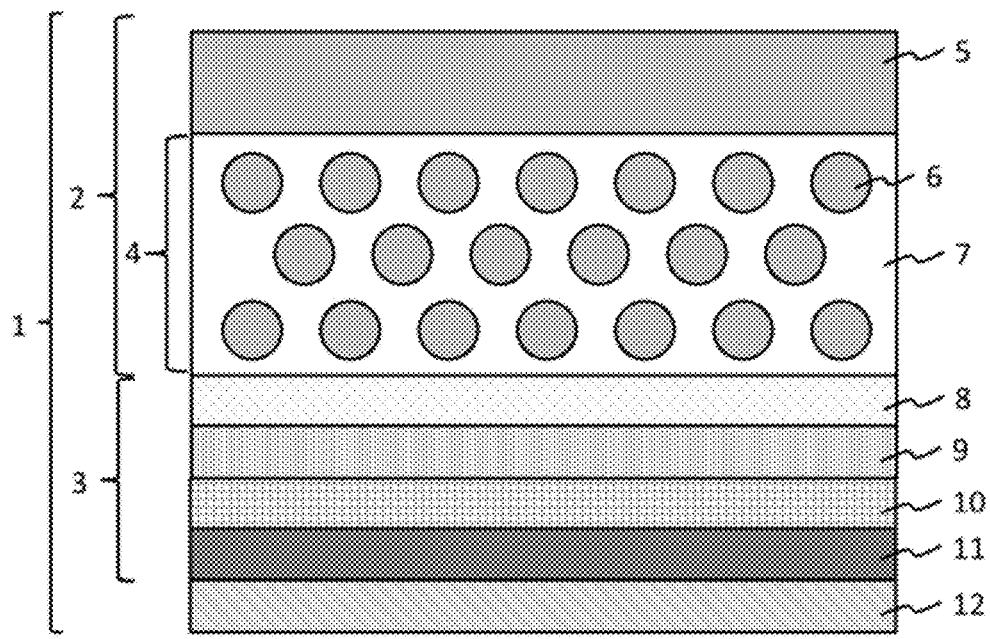
FIG. 1 is a cross-sectional view that schematically depicts one aspect of an X-ray detector containing a scintillator panel according to an embodiment of the present invention.

FIG. 1 schematically depicts one aspect of an X-ray detector containing a scintillator panel according to an embodiment of the present invention. The X-ray detector 1 has a scintillator panel 2, an output board 3, and a power source section 12.

In FIG. 1, the scintillator panel 2 has a base plate 5 and a scintillator layer 4. The scintillator layer 4 contains a phosphor 6, a binder resin 7, a compound represented by the general formula (1) but not depicted here, and/or a salt thereof.

The output board 3 has a photoelectric conversion layer 9 and an output layer 10 on a base plate 11. The photoelectric conversion layer 9 generally has a photosensor and a TFT, which are not depicted here, and is composed of two-dimensionally formed pixels, for example, pixels arranged in matrix form, facing the scintillator layer 4 in the photoelectric conversion layer. The photoelectric conversion layer 9 may have a barrier membrane layer 8 thereon. The light-emitting face of the scintillator panel 2 and the photoelectric conversion layer 9 of the output board 3 are preferably adhered or closely attached to each other via the barrier membrane layer 8.

Figure 2:
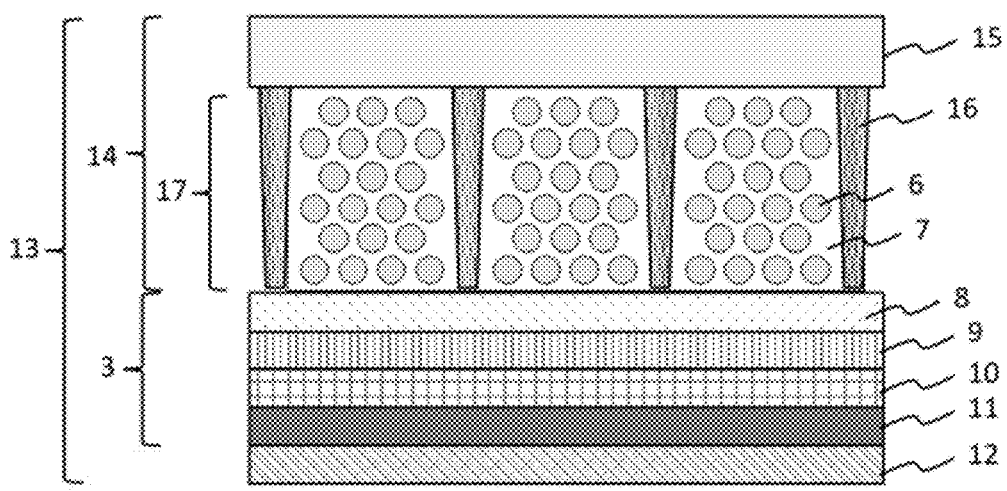
FIG. 2 is a cross-sectional view that schematically depicts one aspect of an X-ray detector containing a scintillator panel having a scintillator layer sectioned with barrier ribs.

FIG. 2 schematically depicts one aspect of an X-ray detector 13 containing a scintillator panel having barrier ribs. The X-ray detector 13 has a scintillator panel 14, an output board 3, and a power source section 12. The scintillator panel 14 has a base plate 15 and a scintillator layer 17, and the scintillator layer 17 is sectioned with barrier ribs 16. The scintillator layer 17 contains a phosphor 6, a binder resin 7, a compound represented by the general formula (1) but not depicted here, and/or a salt thereof. The output board 3 has a photoelectric conversion layer 9 and an output layer 10 on a base plate 11. The photoelectric conversion layer 9 generally has a photosensor and a TFT, which are not depicted here, and is composed of two-dimensionally formed pixels. The photoelectric conversion layer 9 may have a barrier membrane layer 8 thereon.

Light emitted from the scintillator layer 4 or 17 reaches the photoelectric conversion layer 9, photoelectrically converted, and outputted.

A material that constitutes a base plate used in a scintillator panel according to the present invention is preferably radiolucent, and examples of such a material include various glasses, polymer materials, metals, and the like. Examples of glasses include quartz, borosilicate glass, chemically tempered glass, and the like. Examples of polymer materials include: polyesters such as cellulose acetate and polyethylene terephthalate; polyamides; polyimides; triacetates; polycarbonates; carbon-fiber reinforced resins; and the like. Examples of metals include aluminium, iron, copper, and the like. These may be used in combination of two or more kinds thereof. Among these, a polymer material, which has high radiolucency, is particularly preferable. In addition, materials having excellent flatness and heat resistance are preferable.

With reference to the thickness of the base plate, for example, the thickness of a glass base plate is preferably 2.0 mm or less, more preferably 1.0 mm or less, from the viewpoint of decreasing the weight of the scintillator panel. In addition, the thickness of a base plate composed of a polymer material is preferably 3.0 mm or less.

A scintillator panel according to the present invention preferably has a barrier rib sectioning the scintillator layer.

Such a barrier rib is preferably composed of an inorganic substance to have higher strength, durability, and heat resistance. The inorganic substance refers to some kind of simple carbon compound (for example, a carbon allotrope such as graphite, diamond, or the like) or to a compound constituted of an element other than carbon. In this regard, the phrase "composed of an inorganic substance" does not strictly mean the elimination of the possibility of having a component other than an inorganic substance, but permits the presence of an impurity originally contained in the inorganic substance used as a raw material and the presence of a component that is other than the inorganic substance and is contained to the same degree as an impurity leaking into production processes of barrier ribs.

The barrier rib is preferably composed of glass as a main component. The glass refers to an inorganic amorphous solid containing silicate. In cases where the barrier rib is composed of glass as a main component, the barrier rib has higher strength, durability, and heat resistance, and makes it less likely to cause deformation and destruction in the below-mentioned step of forming a reflecting layer and the below-mentioned step of packing a phosphor. In this regard, the phrase "composed of glass as a main component" means that glass accounts for 50 to 100 mass % of the material constituting the barrier rib.

In particular, the barrier rib is such that the ratio of a low-softening-point glass as a glass having a softening point of 650° C. or less is preferably 95 vol % or more, more preferably 98 vol % or more, assuming that the volume of the barrier rib portion is 100 vol %. Containing the low-softening-point glass at a ratio of 95 vol % or more makes it easier to flatten the surface of the barrier rib in a firing step. This makes it easier to form a reflecting layer uniformly on the surface of the barrier rib in the scintillator panel. As a result, the reflectance increases, thus making it possible to further increase the luminance.

Examples of a component that can be used as a component other than a low-softening-point glass include: a high-softening-point glass powder, which is a glass having a softening point of more than 650° C.; a ceramic powder; and the like. These powders make it easier to adjust the shape of the barrier rib in a step of forming the barrier rib. In order to increase the content ratio of the low-softening-point glass, the content ratio of a component other than the low-softening-point glass is preferably less than 5 vol %.

The surface of the barrier rib and the surface of the base plate of the scintillator panel preferably have, thereon, a reflecting layer, particularly a metal reflecting layer. Having a reflecting layer makes it possible that light emitted in a cell by radiation reaches the photoelectric conversion layer efficiently, thus making it easier to enhance luminance.

A material that constitutes the reflecting layer is not limited to any particular material provided that the material functions to reflect electromagnetic waves emitted from the phosphor. Examples of such a material include: metal oxides such as titanium oxide and aluminium oxide; and metals such as silver and aluminium. The material constituting the reflecting layer preferably has high reflectance even in the form of a thin film. Using the material in the form of a thin film makes it possible to inhibit a decrease in the internal volume of the cell and increase the amount of a phosphor to be packed, thus making it easier to enhance the luminance of the scintillator panel. Accordingly, the reflecting layer is preferably made of metal, more preferably silver, aluminium, or an alloy thereof.

The thickness of the reflecting layer can be suitably set in accordance with the necessary reflection characteristics, and is not limited to any particular value. For example, the reflecting layer preferably has a thickness of 10 nm or more, more preferably 50 nm or more. In addition, the reflecting layer preferably has a thickness of 500 nm or less, more preferably 300 nm or less. Allowing the reflecting layer provided on the barrier rib to have a thickness of 10 nm or more makes it possible that the scintillator panel inhibits light from being transmitted by the barrier rib and leaking out, and thus achieves sufficient light shielding, resulting in having higher sharpness. The reflecting layer having a thickness of 500 nm or less makes it less likely to make the roughness of the surface of the reflecting layer large, and to decrease the reflectance.

The scintillator layer used in a scintillator panel according to embodiments of the present invention contains at least a binder resin and a phosphor, and further contains a compound represented by the below-mentioned general formula (1) and/or a salt thereof. The binder resin contained in the scintillator layer is used in an amount sufficient to bind phosphor particles to form the scintillator layer. However, the smaller the amount of the binder resin to be used, the more preferable, from the viewpoint of luminance, provided that the function of the binder is not lost.

Examples of binder resins include thermoplastic resins, thermosetting resins, photo-curing resins, and the like. More specific examples include: acrylic resins; cellulose resins; epoxy resins; melamine resins; phenolic resins; urea resins; vinyl chloride resins; butyral resins; silicone resins; polyester resins such as polyethylene terephthalate and polyethylene naphthalate; polyethylene; polypropylene; polystyrene; polyvinyl toluene; polyphenyl benzene; and the like. These may be contained in combination of two or more kinds thereof. Among these, a resin selected from acrylic resins and butyral resins is preferable.

The binder resin has an influence on the extraction of light from the scintillator layer, and thus, is preferably a very transparent resin because such a resin can further enhance the light extraction efficiency.

Examples of phosphors include inorganic phosphors such as sulfide phosphors, germanate phosphors, halide phosphors, barium sulfate phosphors, hafnium phosphate phosphors, tantalate phosphors, tungstate phosphors, rare earth silicate phosphors, rare earth oxysulfide phosphors, rare earth phosphate phosphors, rare earth oxyhalide phosphors, alkaline earth metal phosphate phosphors, and alkaline earth metal fluorohalide phosphors. Examples of rare earth silicate phosphors include cerium-activated rare earth silicate phosphors. Examples of rare earth oxysulfide phosphors include praseodymium-activated rare earth oxysulfide phosphors, terbium-activated rare earth oxysulfide phosphors, and europium-activated rare earth oxysulfide phosphors. Examples of rare earth phosphate phosphors include terbium-activated rare earth phosphate phosphors. Examples of rare earth oxyhalogen phosphors include terbium-activated rare earth oxyhalide phosphors and thulium-activated rare earth oxyhalide phosphors. Examples of alkaline earth metal phosphate phosphors include europium-activated alkaline earth metal phosphate phosphors. Examples of alkaline earth metal fluorohalide phosphors include europium-activated alkaline earth metal fluorohalide phosphors. Examples of organic phosphors include p-terphenyl, p-quaterphenyl, 2,5-diphenyloxazole, 2,5-diphenyl-1,3,4-oxodiazole, naphthalene, diphenylacetylene, stilbene, and the like. These may be contained in combination of two or more kinds thereof. Among these, a phosphor selected from halide phosphors and rare earth oxysulfide phosphors is preferable. A rare earth oxysulfide phosphor is easy to pack densely, and thus, is more preferably used. Additionally, among rare earth oxysulfides, a gadolinium oxysulfide is easy to pack even more densely, and thus, is preferably used. Such a gadolinium oxysulfide is preferably terbium-activated or europium-activated.

Examples of the shape of the phosphor include particulate shapes, columnar shapes, scaly shapes, and the like. Among these, particulate phosphors are preferable. Using a phosphor in particulate shape causes the phosphor to be dispersed more uniformly in the scintillator layer, thus making it possible to inhibit the ununiformity of light emitted from the phosphor in the scintillator layer, and to emit light uniformly.

The phosphor, preferably an X-ray phosphor, contained in the scintillator layer preferably has an average particle diameter of 0.5 to 50 μm. The phosphor having an average particle diameter of 0.5 μm or more makes it possible to further enhance the efficiency of converting radiation into visible light, and to further enhance the sensitivity. In addition, such an average particle diameter makes it possible to inhibit the agglomeration of the phosphor particles. The phosphor more preferably has an average particle diameter of 3 μm or more, still more preferably 4 μm or more. On the other hand, the phosphor having an average particle diameter of 50 μm or less enables the surface of the scintillator layer to have excellent smoothness, and makes it possible to inhibit a bright spot from being generated on the image. The phosphor more preferably has an average particle diameter of 40 μm or less, still more preferably 30 μm or less, still more preferably 18 μm or less.

Here, the average particle diameter of a phosphor according to the present invention refers to a particle diameter corresponding to 50% in the cumulative distribution of the particle size, and can be measured using a particle size distribution analyzer (for example, MT3300 manufactured by NIKKISO Co., Ltd.). More specifically, an X-ray phosphor is introduced into a sample chamber filled with water, and subjected to ultrasonication for 300 seconds, followed by measurement of a particle size distribution, according to which the particle diameter corresponding to 50% in the cumulative distribution is regarded as the average particle diameter.

A scintillator panel according to an embodiment of the present invention is characterized in that the scintillator layer contains a compound represented by the below-mentioned general formula (1) and/or a salt thereof. The scintillator layer containing the compound represented by the general formula (1) and/or a salt thereof enables a phosphor to be packed densely in the scintillator layer. Allowing the phosphor to be packed more densely enables the thickness of the scintillator layer to be smaller than allowing the phosphor used in the same amount to be packed less densely, and thus, makes it possible to enhance the sharpness with the sensitivity maintained, compared with a system which does not contain any compound represented by the general formula (1) or a salt thereof. In addition, adjusting the thickness of the scintillator layer enables the scintillator panel to have both excellent sensitivity and excellent sharpness, compared with a system which does not contain any compound represented by the general formula (1) and/or a salt thereof.

[Chem. 2]

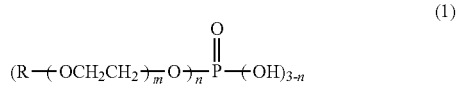

(In the general formula (1), R represents a $C_{1-30}$ hydrocarbon group. m represents an integer of 1 to 20. n represents 1 or 2. When n is 2, a plurality of Rs may be the same or different.)

The compound represented by the general formula (1) has a hydroxyl group as part of the phosphate group, and in addition, may have a salt formed at the hydroxyl group. Although the detailed mechanism is not clear, using such a compound as a compound contained in the scintillator layer makes it easier for the phosphor to be packed densely, and enhances the sensitivity and sharpness.

In the general formula (1), R represents a $C_{1-30}$ hydrocarbon group. Here, in cases where R has a substituent, the carbon number "C" represents the number of carbon atoms including the carbon atoms of the substituent. Examples of hydrocarbon groups include aliphatic hydrocarbon groups and aromatic hydrocarbon groups. Such an aliphatic hydrocarbon group may be linear or branched, and may be partially or wholly cyclic. In addition, the aliphatic hydrocarbon group may be a saturated hydrocarbon group or an unsaturated hydrocarbon group. In the aliphatic hydrocarbon group, at least one of the hydrogen atoms may be substituted with halogen, an aromatic hydrocarbon group, or the like. In addition, the chain may have, for example, an aromatic hydrocarbon group such as a phenylene group. In the aromatic hydrocarbon group, at least one of the hydrogen atoms may be substituted with an aliphatic hydrocarbon group, halogen, or the like. Among these, R is preferably a saturated or unsaturated chain hydrocarbon group. The carbon number of such a hydrocarbon group is preferably 10 or more, more preferably 12 or more. In addition, the carbon number of the hydrocarbon group is preferably 27 or less, more preferably 24 or less, still more preferably 23 or less.

Examples of a salt of a compound represented by the general formula (1) include lithium salts, sodium salts, potassium salts, rubidium salts, cesium salts, magnesium salts, calcium salts, strontium salts, barium salts, ammonium salts, and the like.

A compound represented by the general formula (1) and/or a salt thereof may be physically adsorbed in the surface of the phosphor in the scintillator layer. In addition, the compound and/or a salt thereof may react with the surface of the phosphor to be chemically adsorbed in the surface, or may react with a base eluted from the surface of the phosphor and thus form a salt.

In the general formula (1), m is 1 to 20. When m is 0, the density of the phosphor in the scintillator layer is lower. From the viewpoint of enhancing the density of the phosphor in the scintillator layer, m is preferably 3 or more, more preferably 5 or more, still more preferably 6 or more.

In the general formula (1), n is 1 or 2. Here, when the compound is a salt, the compound may be a metal salt of a multi-charged ion, regardless of the value of n. Unless n is 1 or 2, the density of the phosphor in the scintillator layer is not enhanced.

A compound represented by the general formula (1) and/or a salt thereof can be detected using a general analysis method of organic compounds. For example, the scintillator layer of a scintillator panel is dissolved and dispersed in an organic solvent such as benzyl alcohol, and subjected to centrifugation to sediment the phosphor, followed by detecting the eluted component in the organic solvent using a method such as liquid chromatography mass spectrometry and checking the result with the data in the existing database so that the structure can be identified.

In the scintillator layer, the amount of a compound represented by the general formula (1) and a salt thereof is preferably 0.0001 to 1 wt %. Here, the amount of a compound represented by the general formula (1) and a salt thereof in the scintillator layer refers to the weight fraction of a compound represented by the general formula (1) and a salt thereof to the total weight of the scintillator layer. Here, for supplementary reference, the weight of the scintillator layer does not include the weight of the barrier ribs. Additionally, in cases where the scintillator layer contains one of a compound represented by the general formula (1) and a salt thereof, the amount of the one is determined. In cases where the scintillator layer contains both a compound represented by the general formula (1) and a salt thereof, the amount of these is determined on the basis of the total amount of the compound represented by the general formula (1) and the salt thereof. In cases where the amount of a compound represented by the general formula (1) and a salt thereof is 0.0001 wt % or more, it is easier to recognize that the density of the phosphor in the scintillator layer is enhanced. The amount of a compound represented by the general formula (1) and a salt thereof is preferably 0.001 wt % or more, more preferably 0.003 wt % or more, still more preferably 0.005 wt % or more. Additionally, in cases where the amount of a compound represented by the general formula (1) and a salt thereof is 1 wt % or less, the density of the phosphor is more enhanced. The amount of a compound represented by the general formula (1) and a salt thereof is preferably 0.5 wt % or less, more preferably 0.3 wt % or less, still more preferably 0.2 wt % or less.

The scintillator layer may contain a plurality of a compound(s) represented by the general formula (1) and/or a salt(s) thereof. For example, the scintillator layer may contain a compound of the general formula (1) wherein n is 1 and a compound wherein n is 2. In this case, the amount of a compound(s) represented by the general formula (1) and a salt(s) thereof in the scintillator layer refers to the total amount of a plurality of the compound(s) represented by the general formula (1) and the salt(s) thereof with respect to the total weight of the scintillator layer.

In the present invention, a method of producing a scintillator panel is not limited to any particular method, and examples of such a production method include a method in which a base plate is coated with a phosphor, a binder resin, a compound represented by the general formula (1) and/or a salt, and, if necessary, a phosphor paste containing another component, and, if necessary, the resulting product is dried by heating and/or exposed to light to form a scintillator layer.

Examples of coating methods for a phosphor paste include: screen printing methods; coating methods using a bar coater, roll coater, die coater, blade coater, or the like; and the like. Among these, a roll coater and a die coater are preferably used because these coaters make it easier to perform coating so that the film thickness of the scintillator layer can be uniform even if the layer is a thick film. Among die coaters, a coating method using a slit die coater makes it possible to adjust the thickness of the scintillator layer on the basis of the discharge amount, and to adjust the thickness of the scintillator layer with high precision.

The phosphor paste may contain an organic solvent in addition to the components described above as components for forming the scintillator layer. Such an organic solvent is preferably a good solvent for a binder resin and a compound represented by the general formula (1) and/or a salt thereof, and for a plasticizer, a dispersing agent, and/or the like which is/are to be contained if necessary. Examples of such an organic solvent include ethylene glycol monobutyl ether acetate, diethylene glycol monobutyl ether acetate, ethylene glycol monobutyl ether, diethylene glycol monobutyl ether, triethylene glycol monobutyl ether, polyethylene glycol monobutyl ether, propylene glycol monobutyl ether, dipropylene glycol monobutyl ether, dipropylene glycol monobutyl ether acetate, ethylene glycol phenyl ether, diethylene glycol phenyl ether, isopropyl alcohol, methyl ethyl ketone, cyclohexanone, isobutyl alcohol, isopropyl alcohol, terpineol, benzyl alcohol, tetrahydrofuran, dihydroterpineol, γ-butyrolactone, dihydroterpinyl acetate, 3-methoxy-1-butanol, 3-methoxy-3-methyl-1-butanol, propylene glycol monomethyl ether, propylene glycol monomethyl ether acetate, N,N-dimethylformamide, hexylene glycol, and the like. These may be contained in combination of two or more kinds thereof. Among these, alcohol solvents such as benzyl alcohol are preferable.

In cases where the scintillator panel is produced using a phosphor paste, the amount of a compound represented by the general formula (1) and a salt thereof in the scintillator layer can be adjusted in accordance with the amount of a compound represented by the general formula (1) and a salt thereof in the phosphor paste. In cases where the phosphor paste contains a volatile component such as a solvent, and in cases where the volatile component is removed by drying after the phosphor paste is applied, an adjustment can be made in accordance with the amount of a compound represented by the general formula (1) and a salt thereof with respect to the total amount of the components other than the volatile component in the phosphor paste.

Next, an X-ray detector according to embodiments of the present invention will be described. An X-ray detector according to the present invention can be obtained by disposing the above-mentioned scintillator panel on an output board having a photoelectric conversion layer. The output board has a photoelectric conversion layer and an output layer on a base board. The photoelectric conversion layer generally has a photosensor and a TFT and is composed of two-dimensionally formed pixels.

Next, an X-ray fluoroscopic device according to embodiments of the present invention will be described. An X-ray fluoroscopic device according to embodiments of the present invention has: an X-ray generation unit configured to generate X-rays; and the above-mentioned X-ray detector. The X-ray fluoroscopic device is configured such that a subject is exposed to X-rays from the X-ray generation unit, and that X-rays transmitted through the subject are detected using the X-ray detector. Mounting an X-ray detector according to embodiments of the present invention in the X-ray detection unit makes it possible to obtain an X-ray fluoroscopic device having high sensitivity and high sharpness.

EXAMPLES

Below, the present invention will be described more specifically with reference to Examples and Comparative Examples, but the present invention is not limited by these Examples, and is not construed to be limited to these Examples.

The materials used in Examples and Comparative Examples are enumerated below. In addition, the characteristics of the materials were measured using the below-mentioned methods.

(Average Particle Diameter of X-Ray Phosphor)

An X-ray phosphor was introduced into a sample chamber filled with water in a particle size distribution analyzer (MT3300 manufactured by NIKKISO Co., Ltd.), and subjected to ultrasonication for 300 seconds, followed by measurement of a particle size distribution, according to which the particle diameter corresponding to 50% in the cumulative distribution was regarded as the average particle diameter.

(Raw Material of Phosphor Paste)

Phosphor powder 1: $Gd_2O_2S$:Tb (manufactured by NICHIA CORPORATION; average particle diameter, 11 μm)

Binder resin 1: "S-LEC" (registered trademark) BL-1 (manufactured by SEKISUI CHEMICAL CO., LTD.) polyvinyl butyral Solvent 1: benzyl alcohol Surfactant 1: "PHOSPHANOL" (registered trademark) RS-710 (manufactured by TOHO Chemical Industry Co., Ltd.). This was a compound represented by the general formula (1), and R was a $C_{13}$ aliphatic hydrocarbon group. m was 10. This was a mixture containing a compound wherein n was 1 and a compound wherein n was 2.

Surfactant 2: "PHOSPHANOL" (registered trademark) RS-610 (manufactured by TOHO Chemical Industry Co., Ltd.). This was a compound represented by the above-mentioned general formula (1), and R was a $C_{13}$ aliphatic hydrocarbon group. m was 6. This was a mixture containing a compound wherein n was 1 and a compound wherein n was 2.

Surfactant 3: "PHOSPHANOL" (registered trademark) RS-410 (manufactured by TOHO Chemical Industry Co., Ltd.). This was a compound represented by the above-mentioned general formula (1), and R was a $C_{13}$ aliphatic hydrocarbon group. m was 3. This was a mixture containing a compound wherein n was 1 and a compound wherein n was 2.

Surfactant 4: "PHOSPHANOL" (registered trademark) RM-510 (manufactured by TOHO Chemical Industry Co., Ltd.). This was a compound represented by the above-mentioned general formula (1), and R was a $C_{24}$ aromatic hydrocarbon group substituted with an aliphatic hydrocarbon group. m was 11. This was a mixture containing a compound wherein n was 1 and a compound wherein n was 2.

Surfactant 5: "PLYSURF" (registered trademark) A-219B (manufactured by DKS Co., Ltd.). This was a compound represented by the above-mentioned general formula (1), and R was a $C_{12}$ hydrocarbon group. m was 15. This was a mixture containing a compound wherein n was 1 and a compound wherein n was 2.

Surfactant 6: "PLYSURF" (registered trademark) A-215C (manufactured by DKS Co., Ltd.). This was a compound represented by the above-mentioned general formula (1), and R was a $C_{13}$ unsaturated aliphatic hydrocarbon group. m was 15. This was a mixture containing a compound wherein n was 1 and a compound wherein n was 2.

Surfactant 7: "PHOSPHANOL" (registered trademark) SC-6103 (manufactured by TOHO Chemical Industry Co., Ltd.). This was a calcium salt of a compound represented by the above-mentioned general formula (1), and R was a $C_{13}$ aliphatic hydrocarbon group. m was 6. This was a mixture containing a compound wherein n was 1 and a compound wherein n was 2.

Surfactant 8: "PHOSPHANOL" (registered trademark) RD-720N (manufactured by TOHO Chemical Industry Co., Ltd.). This was a sodium salt of a compound represented by the above-mentioned general formula (1), and R was a $C_{18}$ unsaturated aliphatic hydrocarbon group. m was 7. This was a mixture containing a compound wherein n was 1 and a compound wherein n was 2.

Surfactant 9: "PHOSPHANOL" (registered trademark) ML-200 (manufactured by TOHO Chemical Industry Co., Ltd.). This was a compound represented by the below-mentioned chemical formula (2), and was a mixture containing a compound wherein n was 1 and a compound wherein n was 2.

[Chem. 3]

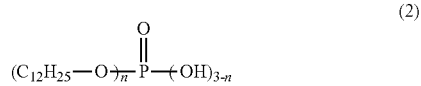

(2)

Surfactant 10: "MEGAFAC" (registered trademark) F-563 (manufactured by DIC Corporation). This was an oligomer containing a fluorine group and a lyophilic group, and was nonionic.

Surfactant 11: "EMULGEN" (registered trademark) 404 (manufactured by Kao Corporation). This had a structure represented by the below-mentioned chemical formula (3).

[Chem. 4]

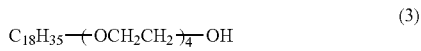

(3)

Plasticizer: TOP (manufactured by DAIHACHI CHEMICAL INDUSTRY Co., Ltd.) Tris(2-ethylhexyl)phosphate Phosphoric acid: phosphoric acid (manufactured by Tokyo Chemical Industry Co., Ltd.)

(Preparation of Binder Resin Solution 1)

Into a stirring container, 20 g of binder resin 1 and 80 g of solvent 1 were added, and the resulting mixture was stirred under heating at 60° C. for eight hours to obtain a binder resin solution 1.

(Raw Material of Glass Powder-Containing Paste)

Photosensitive monomer M-1: trimethylolpropane triacrylate

Photosensitive monomer M-2: tetrapropylene glycol dimethacrylate

Photosensitive polymer 1: a product (weight-average molecular weight, 43000; acid value, 100) obtained by addition reaction of 0.4 equivalents of glycidyl methacrylate with a carboxyl group of a copolymer composed of methacrylic acid/methyl methacrylate/styrene at a mass ratio of 40/40/30

Photo-polymerization initiator 1: 2-benzyl-2-dimethylamino-1-(4-morpholinophenyl) butanone-1 (manufactured by BASF SE)

Polymerization inhibitor 1: 1,6-hexanediol-bis[(3,5-di-t-butyl-4-hydroxyphenyl) propionate])

Ultraviolet ray absorber solution 1: 0.3 mass % γ-butyrolactone solution of Sudan IV (manufactured by TOKYO OHKA KOGYO Co., Ltd.)

Viscosity modifier 1: "FLOWNON" (registered trademark) EC121 (manufactured by KYOEISHA CHEMICAL Co., Ltd.)

Solvent 2: γ-butyrolactone

Low-softening-point glass powder 1:

$SiO_2$, 27 mass %; $B_2O_3$, 31 mass %; ZnO, 6 mass %; $Li_2O$, 7 mass %; MgO, 2 mass %; CaO, 2 mass %; BaO, 2 mass %; $Al_2O_3$, 23 mass %; refractive index (ng) 1.56; glass softening temperature, 588° C.; thermal expansion coefficient, $70 \times 10^{-7}$ ($K^{-1}$); average particle diameter, 2.3 μm (Production of Glass Powder-Containing Paste)

To 38 parts by mass of the solvent 2, 4 parts by mass of the photosensitive monomer M-1, 6 parts by mass of the photosensitive monomer M-2, 24 parts by mass of the photosensitive polymer 1, 6 parts by mass of the photopolymerization initiator 1, 0.2 parts by mass of the polymerization inhibitor 1, and 12.8 parts by mass of the ultraviolet ray absorber solution 1 were added, and the resulting mixture was dissolved under heating at a temperature of 80° C. The resulting solution was cooled, and then, 9 parts by mass of the viscosity modifier 1 was added to the solution to obtain an organic solution 1. To 50 parts by mass of the organic solution 1, 50 parts by mass of the low-softening-point glass powder was added, and then, the resulting mixture was kneaded in a three-roller kneader to obtain a glass powder-containing paste 1.

(Production of Barrier Rib on Base Plate)

A soda glass plate, 125 mm×125 mm×0.7 mm, was used as a base plate. The glass powder-containing paste 1 was applied to the surface of the base plate and dried using a die coater so as to have a thickness of 220 μm after drying, thereby affording a coating film of the glass powder-containing paste 1. Next, the coating film of the glass powder-containing paste 1 was exposed at a dose of 300 mJ/cm² using a super high-pressure mercury lamp via a photomask (chromium mask having grid-like openings and having a pitch of 127 μm and a line width of 15 μm) the openings of which corresponded to a desired pattern. The coating film after exposure was developed in an aqueous solution of 0.5 mass % ethanol amine, and the unexposed portions were removed to obtain a grid-like pattern. The resulting grid-like pattern was fired in the air at 580° C. for 15 minutes to form grid-like barrier ribs the main component of which was glass.

(Formation of Reflecting Layer)

A commercially available sputter device and sputter target were used to form a metal film as a reflecting layer on the base plate having the barrier ribs formed thereon. The metal film was sputtered under conditions where the thickness of the metal film became 300 nm on the flat glass plate that was arranged in the vicinity of the base plate having the barrier ribs formed thereon. For the sputter target, APC (manufactured by Furuya Metal Co., Ltd.) that is a silver alloy containing palladium and copper was used. Hereinafter, this base plate with the barrier ribs having the reflecting layer formed thereon is also referred to as a barrier rib base plate with a reflecting layer.

(Evaluation of Density of Scintillator Layer)

The preliminarily measured weight of the base plate (including a reflecting layer and barrier ribs if these were formed) was subtracted from the weight of the scintillator panel produced in each of Examples and Comparative Examples to determine the weight of the scintillator layer, and this resulting weight was divided by the volume determined by integrating the area of the opposite side of the scintillator layer from the base plate side and the film thickness of the scintillator layer. Thus, the density was calculated. In Examples 1 to 11 and Comparative Examples 2 to 6, relative values were determined with respect to Comparative Example 1 in which the density of the scintillator layer of the scintillator panel was assumed as 100%, and were relatively compared. In Examples 12 to 16 and Comparative Examples 8 and 9, relative values were determine with respect to Comparative Example 7 in which the density of the scintillator layer of the scintillator panel was assumed as 100%, and were relatively compared.

(Evaluation of Sensitivity and Sharpness)

The scintillator panel produced in each of Examples and Comparative Examples was disposed in a commercially available FPD (Paxscan 2520V (manufactured by Varian Medical Systems, Inc.)) to produce an X-ray detector. The base plate side of the scintillator panel was exposed to radiation at a tube voltage of 70 kVp in accordance with the radiation quality RQA5 for evaluating the image quality of a digital image system in the standard IEC62220-1 specified by International Electrotechnical Commission (IEC), and the sensitivity and sharpness of the scintillator panel were thus detected using the FPD. The sensitivity was calculated from the incident dose and the slope of the graph of the digital value of the image. In addition, the sharpness was calculated in accordance with an edge method using a value of 2 cycles/mm. Examples 1 to 11 and Comparative Examples 2 to 6 were relatively compared with respect to Comparative Example 1 in which the sensitivity and the sharpness were each assumed as 100%, and Examples 12 to 16 and Comparative Examples 8 and 9 were relatively compared with respect to Comparative Example 7 in which the sensitivity and the sharpness were each assumed as 100%.

Example 1

To 97.97 parts by weight of the phosphor powder 1, 0.03 parts by weight of the surfactant 1, 10 parts by weight of the binder resin solution 1, and 6 parts by weight of the solvent 1 were added, and the resulting mixture was deaerated with stirring using a planetary mixer/deaerator ("MAZERUSTAR" (registered trademark) KK-400 manufactured by Kurabo Industries Ltd.) at a rotational speed of 1000 rpm for 20 minutes to obtain a phosphor paste 1. The resulting phosphor paste 1 was applied to the PET film of the base plate using a die coater so as to have a film thickness of 200 μm after drying, and dried at 80° C. for four hours to obtain a scintillator panel having a scintillator layer formed on the PET film. The amount of the surfactant contained in the scintillator layer was 0.03 wt %.

The density of the scintillator layer in the resulting scintillator panel was 106%. In addition, the sensitivity was 106%, and the sharpness was 100%.

Example 2

A scintillator panel was produced and evaluated in the same manner as in Example 1 except that the surfactant 2 was used in place of the surfactant 1 in Example 1. The amount of the surfactant contained in the scintillator layer was 0.03 wt %.

The density of the scintillator layer in the resulting scintillator panel was 105%. In addition, the sensitivity was 105%, and the sharpness was 100%.

Example 3

A scintillator panel was produced and evaluated in the same manner as in Example 1 except that the surfactant 3 was used in place of the surfactant 1 in Example 1. The amount of the surfactant contained in the scintillator layer was 0.03 wt %.

The density of the scintillator layer in the resulting scintillator panel was 102%. In addition, the sensitivity was 102%, and the sharpness was 100%.

Example 4

A scintillator panel was produced and evaluated in the same manner as in Example 1 except that the surfactant 4 was used in place of the surfactant 1 in Example 1. The amount of the surfactant contained in the scintillator layer was 0.03 wt %.

The density of the scintillator layer in the resulting scintillator panel was 104%. In addition, the sensitivity was 104%, and the sharpness was 100%.

Example 5

A scintillator panel was produced and evaluated in the same manner as in Example 1 except that the surfactant 5 was used in place of the surfactant 1 in Example 1. The amount of the surfactant contained in the scintillator layer was 0.03 wt %.

The density of the scintillator layer in the resulting scintillator panel was 106%. In addition, the sensitivity was 106%, and the sharpness was 100%.

Example 6

A scintillator panel was produced and evaluated in the same manner as in Example 1 except that the surfactant 6 was used in place of the surfactant 1 in Example 1. The amount of the surfactant contained in the scintillator layer was 0.03 wt %.

The density of the scintillator layer in the resulting scintillator panel was 106%. In addition, the sensitivity was 106%, and the sharpness was 100%.

Example 7

A scintillator panel was produced and evaluated in the same manner as in Example 1 except that the surfactant 7 was used in place of the surfactant 1 in Example 1. The amount of the surfactant contained in the scintillator layer was 0.03 wt %.

The density of the scintillator layer in the resulting scintillator panel was 105%. In addition, the sensitivity was 105%, and the sharpness was 100%.

Example 8

A scintillator panel was produced and evaluated in the same manner as in Example 1 except that the surfactant 8 was used in place of the surfactant 1 in Example 1. The amount of the surfactant contained in the scintillator layer was 0.03 wt %.

The density of the scintillator layer in the resulting scintillator panel was 105%. In addition, the sensitivity was 105%, and the sharpness was 100%.

Example 9

A scintillator panel was produced and evaluated in the same manner as in Example 1 except that the phosphor paste 1 in Example 1 was applied to the PET film of the base plate so as to have a film thickness of 195 μm after drying. The amount of the surfactant contained in the scintillator layer was 0.03 wt %.

The density of the scintillator layer in the resulting scintillator panel was 106%. In addition, the sensitivity was 103%, and the sharpness was 102%.

Example 10

A scintillator panel was produced and evaluated in the same manner as in Example 1 except that 97.7 parts by weight of the phosphor powder 1, 0.3 parts by weight of the surfactant 1, 10 parts by weight of the binder resin solution 1, and 6 parts by weight of the solvent 1 were added and mixed to prepare a phosphor paste. The amount of the surfactant contained in the scintillator layer was 0.3 wt %.

The density of the scintillator layer in the resulting scintillator panel was 102%. In addition, the sensitivity was 102%, and the sharpness was 100%.

Example 11

A scintillator panel was produced and evaluated in the same manner as in Example 1 except that 97.997 parts by weight of the phosphor powder 1, 0.003 parts by weight of the surfactant 1, 10 parts by weight of the binder resin solution 1, and 6 parts by weight of the solvent 1 were added and mixed to prepare a phosphor paste. The amount of the surfactant contained in the scintillator layer was 0.003 wt %.

The density of the scintillator layer in the resulting scintillator panel was 102%. In addition, the sensitivity was 102%, and the sharpness was 100%.

Comparative Example 1

A scintillator panel was produced and evaluated in the same manner as in Example 1 except that 98 parts by weight of the phosphor powder 1, 10 parts by weight of the binder resin solution 1, and 6 parts by weight of the solvent 1 were added without using the surfactant 1, and mixed to prepare a phosphor paste.

The density of the scintillator layer in the resulting scintillator panel was 100%. In addition, the sensitivity was 100%, and the sharpness was 100%.

Comparative Example 2

A scintillator panel was produced and evaluated in the same manner as in Example 1 except that the surfactant 9 having no polyethylene oxide chain was used in place of the surfactant 1 in Example 1. The amount of the surfactant contained in the scintillator layer was 0.03 wt %.

The density of the scintillator layer in the resulting scintillator panel was 96%. In addition, the sensitivity was 96%, and the sharpness was 100%.

Comparative Example 3

A scintillator panel was produced and evaluated in the same manner as in Example 1 except that the fluorine surfactant 10 was used in place of the surfactant 1 in Example 1. The amount of the surfactant contained in the scintillator layer was 0.03 wt %.

The density of the scintillator layer in the resulting scintillator panel was 99%. In addition, the sensitivity was 99%, and the sharpness was 100%.

Comparative Example 4

A scintillator panel was produced and evaluated in the same manner as in Example 1 except that the surfactant 11 having no phosphate group was used in place of the surfactant 1 in Example 1. The amount of the surfactant contained in the scintillator layer was 0.03 wt %.

The density of the scintillator layer in the resulting scintillator panel was 97%. In addition, the sensitivity was 97%, and the sharpness was 100%.

Comparative Example 5

A scintillator panel was produced and evaluated in the same manner as in Example 1 except that phosphoric acid triester as a plasticizer was used in place of the surfactant 1 in Example 1. The amount of the plasticizer contained in the scintillator layer was 0.03 wt %.

The density of the scintillator layer in the resulting scintillator panel was 99%. In addition, the sensitivity was 99%, and the sharpness was 100%.

Comparative Example 6

A scintillator panel was produced and evaluated in the same manner as in Example 1 except that phosphoric acid was used in place of the surfactant 1 in Example 1. The amount of the phosphoric acid contained in the scintillator layer was 0.03 wt %.

The density of the scintillator layer in the resulting scintillator panel was 100%. In addition, the sensitivity was 100%, and the sharpness was 100%.

Example 12

A phosphor paste 1 was produced in the same manner as in Example 1, and the resulting phosphor paste 1 was packed in the above-mentioned barrier rib base plate with a reflecting layer by vacuum printing, and dried at 150° C. for 15 minutes to form a scintillator layer. The amount of the surfactant contained in the scintillator layer was 0.03 wt %.

The density of the scintillator layer in the resulting scintillator panel was 107%. In addition, the sensitivity was 107%, and the sharpness was 100%.

Example 13

A scintillator panel was produced and evaluated in the same manner as in Example 12 except that the surfactant 4 was used in place of the surfactant 1 in Example 12. The amount of the surfactant contained in the scintillator layer was 0.03 wt %.

The density of the scintillator layer in the resulting scintillator panel was 104%. In addition, the sensitivity was 104%, and the sharpness was 100%.

Example 14

A scintillator panel was produced and evaluated in the same manner as in Example 12 except that the surfactant 5 was used in place of the surfactant 1 in Example 12. The amount of the surfactant contained in the scintillator layer was 0.03 wt %.

The density of the scintillator layer in the resulting scintillator panel was 107%. In addition, the sensitivity was 107%, and the sharpness was 100%.

Example 15

A scintillator panel was produced and evaluated in the same manner as in Example 12 except that the surfactant 6 was used in place of the surfactant 1 in Example 12. The amount of the surfactant contained in the scintillator layer was 0.03 wt %.

The density of the scintillator layer in the resulting scintillator panel was 107%. In addition, the sensitivity was 107%, and the sharpness was 100%.

Example 16

A scintillator panel was produced and evaluated in the same manner as in Example 12 except that the surfactant 8 was used in place of the surfactant 1 in Example 12. The amount of the surfactant contained in the scintillator layer was 0.03 wt %.

The density of the scintillator layer in the resulting scintillator panel was 106%. In addition, the sensitivity was 105%, and the sharpness was 100%.

Comparative Example 7

A scintillator panel was produced and evaluated in the same manner as in Example 12 except that 98 parts by weight of the phosphor 1, 10 parts by weight of the binder resin solution 1, and 6 parts by weight of the solvent 1 were added without using the surfactant 1, and mixed to prepare a phosphor paste.

The density of the scintillator layer in the resulting scintillator panel was 100%. In addition, the sensitivity was 100%, and the sharpness was 100%.

Comparative Example 8

A scintillator panel was produced and evaluated in the same manner as in Example 12 except that the surfactant 9 was used in place of the surfactant 1 in Example 12. The amount of the surfactant contained in the scintillator layer was 0.03 wt %.

The density of the scintillator layer in the resulting scintillator panel was 95%. In addition, the sensitivity was 95%, and the sharpness was 100%.

Comparative Example 9

A scintillator panel was produced and evaluated in the same manner as in Example 12 except that the surfactant 11 was used in place of the surfactant 1 in Example 12. The amount of the surfactant contained in the scintillator layer was 0.03 wt %.

The density of the scintillator layer in the resulting scintillator panel was 96%. In addition, the sensitivity was 96%, and the sharpness was 100%.

REFERENCE SIGNS LIST

1 X-Ray Detector
2 Scintillator Panel
3 Output Board
4 Scintillator Layer
5 Base Plate
6 Phosphor
7 Binder Resin
8 Barrier Membrane Layer
9 Photoelectric Conversion Layer
10 Output Layer
11 Base Plate
12 Power Source Section
13 X-Ray Detector
14 Scintillator Panel
15 Base Plate
16 Barrier Rib
17 Scintillator Layer

The invention claimed is:

1. A scintillator panel comprising a base plate and a scintillator layer containing a binder resin and a phosphor, said scintillator layer further containing a compound represented by the following general formula (1) and/or a salt thereof;

[Chem. 1]

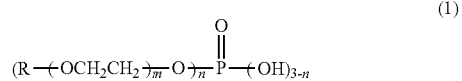

(1)

wherein, in the general formula (1), R represents a $C_{1-30}$ hydrocarbon group; m represents an integer of 1 to 20; n represents 1 or 2; and when n is 2, a plurality of Rs may be the same or different).

2. The scintillator panel according to claim 1, wherein the amount of said compound represented by the general formula (1) and a salt thereof in said scintillator layer is 0.0001 to 1 wt %.

3. The scintillator panel according to claim 1, wherein said phosphor contains gadolinium oxysulfide.

4. The scintillator panel according to claim 1, comprising a barrier rib sectioning said scintillator layer.

5. An X-ray detector comprising said scintillator panel according to claim 1 and an output board having a photoelectric conversion layer.

6. An X-ray fluoroscopic device comprising said X-ray detector according to claim 5 mounted therein.

* * * * *